(12) United States Patent
Wang et al.

(10) Patent No.: US 7,615,758 B2
(45) Date of Patent: Nov. 10, 2009

(54) LASER CONFOCAL MICROARRAY SCANNER

(75) Inventors: Xianhua Wang, Beijing (CN); Hui Xu, Beijing (CN); Jianxin Ye, Beijing (CN); Yelei Sun, Beijing (CN); Guoliang Huang, Beijing (CN); Jing Cheng, Beijing (CN)

(73) Assignee: Capitalbio Corporation, Beijing (CN)

( * ) Notice: Subject to any disclaimer, the term of this patent is extended or adjusted under 35 U.S.C. 154(b) by 0 days.

(21) Appl. No.: 11/795,660

(22) PCT Filed: Jun. 2, 2005

(86) PCT No.: PCT/CN2005/000771

§ 371 (c)(1),
(2), (4) Date: May 16, 2008

(87) PCT Pub. No.: WO2006/128321

PCT Pub. Date: Dec. 7, 2006

(65) Prior Publication Data

US 2008/0252954 A1  Oct. 16, 2008

(51) Int. Cl.
*F21V 9/16* (2006.01)
(52) U.S. Cl. ................................... 250/458.1
(58) Field of Classification Search ............. 250/458.1, 250/461.2
See application file for complete search history.

(56) References Cited

U.S. PATENT DOCUMENTS

| 4,557,154 | A | 12/1985 | Iwata et al. |
| 6,355,934 | B1 | 3/2002 | Osgood et al. |
| 6,471,916 | B1 | 10/2002 | Noblett |
| 6,740,871 | B1 | 5/2004 | Staton et al. |
| 2002/0062202 | A1 | 5/2002 | Arai |
| 2003/0030850 | A1* | 2/2003 | Heffelfinger et al. ........ 358/474 |
| 2003/0161514 | A1 | 8/2003 | Curry |
| 2003/0164814 | A1 | 9/2003 | Starkweather et al. |
| 2004/0042007 | A1* | 3/2004 | Osipchuk et al. ............ 356/318 |

FOREIGN PATENT DOCUMENTS

| CN | 2290063 Y | 9/1998 |
| CN | 1387824 A | 1/2003 |
| CN | 1534288 A | 10/2004 |
| JP | 11014609 A | 1/1999 |
| JP | 2002-098639 A | 4/2002 |
| JP | 2003-015442 A | 1/2003 |
| WO | WO-2006/128321 A1 | 12/2003 |
| WO | WO-2006/128322 A1 | 12/2003 |

OTHER PUBLICATIONS

U.S. Appl. No. 11/795,652, filed Jun. 2, 2005, by Wang et al.

* cited by examiner

*Primary Examiner*—David P Porta
*Assistant Examiner*—Kiho Kim
(74) *Attorney, Agent, or Firm*—Morrison & Foerster LLP (57) ABSTRACT

The invention provides a laser microarray scanner for microarray scanning, comprising an optical system, a scanning platform, and a data processing system. During scanning, the optical system remains fixed, and the microarray placed on the scanning platform moves relative to the optical system. The microarray scanner disclosed herein has high scanning speed, high sensitivity, high resolution, and high signal-to-noise ratio, thus is ideal for use in microarray scanning

28 Claims, 2 Drawing Sheets

LASER CONFOCAL MICROARRAY SCANNER

TECHNICAL FIELD

This application is in the field of detection devices for microarrays, particularly in the filed of laser microarray scanner for scanning high density microarrays.

BACKGROUND OF THE INVENTION

Developments in microarray-based detection devices have dramatically changed the biotechnology industry. The devices make it possible to analyze multiple biological samples simultaneously and detect rare transcripts in human. They also make it possible to obtain information from microarrays automatically within minutes instead of within months or even years without the help of the devices.

Microarrays typically comprise a plurality of polymers, such as oligonucleotides, peptides, and antibodies. The polymers are synthesized or deposited on a substrate in an array pattern, which can be labeled with optically detectable labels such as fluorescent tags or fluorophores. A typical microarray scanner uses laser as excitation light source, and use matching filters and photomultiplier tubes for detection. During scanning of a microarray, excitation light from the laser source hits different spots on the microarray. Fluorescent probes on the array emit Stokes-shifted light in response to the excitation light, and the emission light is collected by the photomultiplier tube. The resulting information on the microarray can be used for various purposes such as gene expression studies, mutational studies, genotyping, SNP studies, protein interaction analysis, as well as diagnosis and treatment of diseases.

As microarray technologies develop, there is a need for new fluorescent light-based microarray scanners, particularly microarray scanners with high scanning speed, high sensitivity, and low cost.

BRIEF SUMMARY OF THE INVENTION

In one aspect, the invention provides a laser microarray scanner comprising an optical system, a scanning platform and a data processing system, wherein the optical system comprises an aperture-containing reflecting mirror comprising an aperture and a reflecting surface, wherein the aperture on the aperture-containing reflecting mirror allows an excitation light to pass through and wherein the reflecting surface of the aperture-containing reflecting mirror allows emission light from a microarray to be reflected. In some embodiments, the optical system of the microarray scanner further comprises an excitation objective lens for focusing the excitation light passing through the aperture-containing reflecting mirror.

In some embodiments, the optical system of the microarray scanner further comprises a light forwarding system for generating the excitation light. The light forwarding system may comprise a first laser generator (with an optional light filter), a second laser generator (with an optional light filter), a beam splitter, and a light chopper, wherein the beam splitter transmits laser light generated by the first laser generator and reflects laser light generated by the second laser generator, and wherein the light chopper allows laser light generated by one laser generator to go through while blocking laser light generated by another laser generator at each time.

In some embodiments, the light forwarding system of the optical system further comprises a first reflecting mirror optically positioned between the first laser generator and the beam splitter and a second reflecting mirror optically positioned between the beam splitter and the aperture-containing reflecting mirror, wherein light generated by the first laser generator is first reflected by the first reflecting mirror before it is transmitted by the beam splitter, and wherein light coming from the beam splitter is first reflected by the second reflecting mirror before it passes through the aperture of the aperture-containing reflecting mirror. In some embodiments, the optical system further comprises an attenuator, wherein the attenuator is optically positioned behind the beam splitter so that light coming from the beam splitter can be adjusted by the attenuator.

In some embodiments, the optical system of the microarray scanner further comprises a light collection system for collecting the emission light, wherein the light collection system comprises a detector (such as a photomuliplier tube) and an emission objective lens optically positioned between the detector and the aperture-containing reflecting mirror. In some embodiments, the light collection system of the optical system further comprises a pinhole optically positioned between the emission objective lens and the detector.

In some embodiments, the light collection system further comprises an emission light filter optically positioned between the aperture-containing reflecting mirror and the emission objective lens. The emission light filter may comprise a single light filter or multiple light filters (such as 2, 3, 4, 5, 6, 7, 8, 9, or 10 filters) for filtering light of different wavelengths.

In one embodiment, the optical system comprises an aperture-containing reflecting mirror comprising an aperture and a reflecting surface; an excitation objective lens; a light forwarding system comprising a first laser generator; a first reflecting mirror that reflects light generated by the first laser generator; a second laser generator; a beam splitter that transmits light reflected by the first reflecting mirror and reflects light generated by the second laser generator; a light chopper that allows light generated by one laser generator to go through while blocking light generated by another laser generator at a given time; and a second reflecting mirror that reflects the light allowed to go through, wherein light reflected by the second reflecting mirror passes through the aperture of the aperture-containing reflecting mirror and is focused by the objective lens; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector. In some embodiments, the optical system further comprises matching light filter optically positioned in front of at least one of the two laser generators. In some embodiments, the optical system further comprises an attenuator optically positioned between the beam splitter and the second reflecting mirror.

In some embodiments, the scanning platform of the microarray scanner comprises any of the optical systems described herein, a data processing system, and a scanning platform comprising a stage coupled to a scanning driving mechanism that drives movement of the stage in the scanning direction and a forwarding driving mechanism that drives movement of the stage in the forwarding direction. The scanning driving mechanism can comprise, for example, a wheel and a flexible metal strip winding around the wheel, wherein two regions of the stage are affixed to the stage so that rotation of the wheel moves the stage.

In another aspect, the invention provides a laser microarray scanner comprising an optical system, a scanning platform, and a data processing system, wherein the scanning platform comprises a stage for placing a microarray, wherein the stage is controlled by a first driving mechanism comprising a wheel and a flexible metal strip winding around the wheel, wherein two regions of the flexible metal strip are affixed to the stage so that rotation of the wheel moves the stage. In some embodiments, the wheel is actuated by a servo motor with low inertia. In some embodiments, one of the two regions of the flexible metal strip is releasably affixed to the stage. In some embodiments, the flexible metal strip further comprises a prefastening region extending beyond the region that is releasably affixed to the stage.

In some embodiments, the scanning platform of the microarray scanner further comprises a second driving mechanism, wherein the first driving mechanism moves the stage in a scanning direction and wherein the second driving mechanism moves the stage in a forwarding direction that is different from (such as perpendicular to) the scanning direction. In some embodiments, the first driving mechanism is positioned below the stage and above the second driving mechanism. In some embodiments, the second driving mechanism comprises a lead screw coupled to a stepper motor.

In another aspect, the invention provides a laser microarray scanner comprising an optical system, a scanning platform, and a data processing system, wherein the scanning platform comprises a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail. In some embodiments, the scanning driving mechanism of the scanning platform comprises a wheel and a flexible metal strip winding around the wheel, wherein two regions of the flexible metal strip are affixed to the stage so that rotation of the wheel moves the stage. In some embodiments, the scanning driving mechanism is actuated by a servo motor with low inertia. In some embodiments, the scanning driving mechanism is mounted on the slider. In some embodiments, the forwarding driving mechanism comprises a lead screw coupled to a stepper motor.

In one embodiment, the laser microarray scanner comprises an optical system, a scanning platform, and a data processing system, wherein the scanning platform comprises a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism. The scanning driving mechanism may be mounted on the slider. In some embodiments, one of the two regions of the flexible metal strip is releasably affixed to the stage. In some embodiments, the flexible metal strip further comprises a prefastening region extending beyond the region that is releasably affixed to the stage.

In some embodiments, the microarray scanner comprises any of the laser platforms described herein, a data processing system, and an optical system comprising a light forwarding system comprising a first laser generator, a second laser generator, a beam splitter, and a light chopper, wherein the beam splitter transmits laser light generated by the first laser generator and reflects laser light generated by the second laser generator, and wherein the light chopper allows laser light generated by one laser generator to go through while blocking laser light generated by another laser generator at each time.

In some embodiments, the microarray scanner comprises any of the laser platforms described herein, a data processing system, and an optical system comprising a light collection system comprising an emission filter, an emission objective lens optically positioned behind the emission filter, a pinhole optically positioned behind the emission objective lens, and a detector optically positioned behind the pinhole, wherein the emission light passes the emission filter, emission objective lens, and pinhole sequentially before it reaches the detector.

DETAILED DESCRIPTION OF THE INVENTION

The present invention provides a laser microarray scanner comprising an optical system and a scanning platform. During operation of the microarray scanner, the optical system remains fixed. The microarray placed on the stage of the scanning platform moves in any desired direction in a two-dimensional plane relative to the optical system, so that the whole microarray is scanned. In some embodiments, the scanner further comprises a data processing system for data processing and collection.

Some or all of the different systems of the microarray scanner may be controlled by computers. The data processing system may be an integrated part of the microarray scanner. Alternatively, some components of the data processing system may be separated from the rest of the scanner (such as a personalized computer, a work station, etc.). Accordingly, in one embodiment, the present invention provides an integrated and/or automated microarray scanner.

The microarray scanners disclosed herein provide high scanning speed, high sensitivity, high resolution, and high signal to noise ratio, and can be used for scanning any kind of microarrays, including, but not limited to, arrays of DNA, RNA, cDNA, polynucleotides, oligonucleotides, proteins, peptides, and antibodies. Information obtained from the microarray scanning can be useful for various purposes such as gene expression studies, mutational studies, genotyping, SNP studies, protein interaction analysis, as well as diagnosis and treatment of diseases.

Optical Systems for the Microarray Scanner

The optical system of the microarray scanner of the present invention generates excitation light for scanning the microarray and collects light emitted from the microarray. The optical system may comprise a novel optical system described in patent application entitled "Optical Systems for Microarray Scanning,", incorporated entirely herein by references.

In some embodiment, the optical system comprises an aperture-containing reflecting mirror, which comprises an aperture that allows an excitation light to directly pass through and a reflecting surface that allows emission light from a microarray to be reflected. The optical system may further comprise an excitation objective lens for focusing the excitation light passing through the aperture of the aperture-containing reflecting mirror and/or collimating emission light from the microarray. In some embodiments, the excitation objective lens is connected to a motor (such as a stepper motor), which moves the objective lens in a direction perpendicular to the surface of the microarray. The position of the objective lens can thus be adjusted in order to focus the excitation light.

Use of the aperture-containing reflecting mirror of the present invention greatly increases the efficiency of the optical system, reduces background noise, and eliminates mutual interference between the excitation light and the emission light. During scanning of a microarray, the excitation light passes through the aperture of the aperture-containing reflecting mirror and becomes directly focused on the microarray to be scanned. Fluorescent light emitted from fluorophores on the microarray is then reflected by the reflecting surface of the aperture-containing reflecting mirror and becomes collected. The excitation light passes the aperture of the aperture-containing reflecting mirror without encountering any blockage, thus reduces light loss. Furthermore, most of the background light reflected from the microarray chip is transmitted through the aperture and does not enter the light collection system. Accordingly, signal-to-noise ratio can be improved.

The aperture of the aperture-containing reflecting mirror can be of any shape, including, but not limited to, circle, oval, square, rectangle, triangle, or other regular or irregular shapes. The dimension of the aperture can be within any practical range that allows the passage of the excitation light without blockage. For example, when the aperture is a circle, its diameter can (but not necessarily) be between about 0.5 mm to about 5 mm, such as between about 0.8 mm to about 0.4 mm, such as between about 1 mm and about 3 mm, such as about 3 mm.

The aperture-containing reflecting mirror can be of any shape, including, but not limited to, circle, oval, square, rectangle, triangle, or other regular or irregular shapes. The reflecting mirror can be tilted at any angle relative to the surface of the microarray to be scanned, such as about any of 15°, 20°, 30°, 40°, 45°, 50°, or 60° relative to the surface of the microarray to be scanned.

The optical system may also comprise a light forwarding system or generating the excitation light. In some embodiments, the light forwarding system of the optical system comprises a laser generator and optionally a reflecting mirror. For example, when used in combination with an aperture-containing reflecting mirror, light generated from the laser generator is optionally reflected by the reflecting mirror, and the light (reflected or not reflected) passes directly through the aperture of the aperture-containing reflecting mirror. The light forwarding system may further comprise a matching light filter optically positioned in front of the first laser generator, which is used to filter the light generated by the laser generator into narrow-band excitation light.

In some embodiments, the light forwarding system of the optical system comprises a first laser generator (with an optional matching light filter), a second laser generator (with an optional matching filter), a beam splitter, and a light chopper. The two laser generators typically generate light of different wavelengths. The beam splitter is optically positioned so that light generated by the first laser generator is transmitted and light generated by the second laser generator is reflected. The light chopper is optically positioned next to the beam splitter. It allows light generated by one laser generator to go through while blocking light generated by another laser generator at any given time, thus ensures that only one kind of light enters the excitation light path. Use of the light chopper avoids traditional use of rotating reflecting mirrors for selecting laser sources, and thus ensures stability of the optical system.

The optical system (such as the light forwarding system of the optical system) may further comprise one or more reflecting mirrors. The reflecting mirrors are used to alter the direction of the light path, and can be used in any desired manner. For example, there may be a first reflecting mirror optically positioned between the first laser generator and the beam splitter. Light generated by the first laser generator is first reflected by the first reflecting mirror before encountering the beam splitter. In some embodiments, when used in combination with an aperture-containing reflecting mirror, the light forwarding system may further comprise a second reflecting mirror (preferably a proportional reflecting mirror) optically positioned between the beam splitter and the aperture-containing reflecting mirror. Light coming from the beam splitter/light chopper can first be reflected by the second reflecting mirror before it passes directly through the aperture of the aperture-containing reflecting mirror. There can also be a light intensity detector optically positioned to detect light transmitted by the second reflecting mirror. Light signals detected by the light intensity detector can be further converted into digital signals, which can be used to indicate the intensity of the excitation light.

The light forwarding system of the optical system may further comprise an attenuator for controlling and adjusting light intensity of the excitation light. The attenuator may be optically positioned immediately behind the beam splitter so that light combing from the aperture-containing reflecting mirror is adjusted by the attenuator.

As in known in the art, when excitation light scans the microarray, fluorophores on the microarray produce Stoke-shifted emission light in response to the excitation light, which can be collected by a light collection system. Accordingly, the optical system may also comprise a light collection system for collecting emission light from the microarray. The light collection system of the optical system may comprise a detector and an emission objective lens. In some embodiments, the detector is a photomultiplier tube (PMT). The PMT converts incident photons into electrons via the photoelectric effect. A photon strikes the active surface of the PMT (the photocathode), generating an electron. The electron flows through a series of dynodes that multiply the electrons until they reach the anode. The resulting current from the anode is directly proportional to the incident light at the photocathode. The electrical signal can be further amplified by an amplifying filter and converted into digital signals for computer analysis.

In some embodiments, the light collection system of the optical system further comprises a pinhole optically positioned between the emission objective lens and the detector. The pinhole is placed in front of the detector, such that fluorescent light from the microarray that is not within the focal plane where the laser beam was focused (i.e., out-of-focus light) is largely obstructed by the pinhole. In this way, out-of-focus information is greatly reduced.

In some embodiments, the light collection system of the optical system further comprises an emission light filter optically positioned in front of the emission objective lens so that only light of a desired wavelength passes through the emission objected lens and become detected. In some embodiments, the emission light filter comprises two or more (such as 2, 3, 4, 5, 6, 7, 8, 9, 10, or more) light filters for filtering light of different wavelengths (i.e., each allowing light of a different wavelength to pass through). These multiple filters can be arranged in any practical ways. For example, the multiple filters in the emission light filter can be in a circular arrangement (such as in a wheel), and the desired filter is chosen by rotating the emission light filter (i.e., the wheel) so that the desired light filter is optically positioned in the light path.

The choice of the emission light filter(s) depends on the wavelength of the excitation light and the excitation/emission light spectrum of the fluorophores to be detected. The combination of the two laser generators with different matching emission light filters thus allows detection of multiple fluorophores in a sample, either sequentially or simultaneously. Therefore, multiple labels of a sample can be detected using the optical system of the present invention. This is particularly useful in microarray scanning, where multiple probes labeled with different markers are typically used and need to be detected.

In one embodiment, the optical system comprises an aperture-containing reflecting mirror comprising an aperture and a reflecting surface; an excitation objective lens; a light forwarding system comprising a first laser generator; a first reflecting mirror that reflects light generated by the first laser generator; a second laser generator; a beam splitter that transmits light reflected by the first reflecting mirror and reflects light generated by the second laser generator; a light chopper that allows light generated by one laser generator to go through while blocking light generated by another laser generator at a given time; and a second reflecting mirror that reflects the light allowed to go through, wherein light reflected by the second reflecting mirror passes through the aperture of the aperture-containing reflecting mirror and is focused by the objective lens; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector. In some embodiments, the optical system further comprises matching light filter optically positioned in front of at least one of the two laser generators. In some embodiments, the optical system further comprises an attenuator optically positioned between the beam splitter and the second reflecting mirror.

In another aspect, the invention provides an optical system comprising (such as consisting of or consisting essentially of) a first laser generator, an aperture-containing reflecting mirror, an excitation objective lens, an emission objective lens, a pinhole, and a detector, wherein the components of the optical system are optically connected. Specifically, light generated by the laser generator passes through the aperture of the aperture-containing mirror, and is focused on the microarray to be scanned by the excitation objective lens. Upon excitation, fluorophores on the microarray to be scanned emit fluorescent light. The emitted light is then collimated by the excitation objective lens and reflected by the aperture-containing reflecting mirror. The reflected emission light passes through the emission objective lens and then the pinhole and is collected by the detector.

In some embodiments, the optical system further includes a second laser generator, a beam splitter and a light chopper. Light generated by the first laser generator is transmitted by the beam splitter, while light generated by the second laser generator is reflected by the beam splitter. The light chopper allows light generated by one laser generator to go through while blocking light generated by another generator at a given time.

In some embodiments, the optical system further includes a first reflecting mirror optically positioned between the first laser generator and the beam splitter. Light generated by the first laser generator is first reflected by the first reflecting mirror before encountering the beam splitter. In some embodiments, there may be a second reflecting mirror (preferably a proportional reflecting mirror) optically positioned between the beam splitter and the aperture-containing reflecting mirror. Light coming from the beam splitter/light chopper can first be reflected by the second reflecting mirror before it passes directly through the aperture of the aperture-containing reflecting mirror. In some embodiments, the optical system may also comprise a light intensity detector that detects light transmitted by the second reflecting mirror.

In some embodiments, the optical system further includes an attenuator optically positioned between the beam splitter and the second reflecting mirror. In some embodiments, the optical system further includes matching light filter placed immediately in front of at least one of the laser generators. In some embodiments, the optical system further includes an emission light filter (such as two or more light filters for filtering light of different wavelength in a complex emission filter) optically positioned between the aperture-containing reflecting mirror and the emission objective lens.

In another aspect, the optical system comprises (such as consists of or consisting essentially of) a first laser generator, a first excitation light filter, a first reflecting mirror, a second laser generator, a second excitation light filter, a beam splitter, a light chopper, a second reflecting mirror, an aperture-containing reflecting mirror, an excitation objective lens, an emission light filter, an emission objective lens, a pinhole, and a detector, wherein the components of the optical system are optically connected.

In some embodiment, the optical system comprises (such as consists of or consists essentially of) a first laser generator, a first excitation light filter, a first reflecting mirror, a second laser generator, a second excitation light filter, a beam splitter, a light chopper, a second reflecting mirror, an aperture-containing reflecting mirror, an excitation objective lens, an emission light filter, an emission objective lens, a pinhole, and a detector, wherein light generated by the first laser generator is filtered by the first excitation light filter, reflected by the first reflecting mirror and transmitted by the beam splitter; wherein laser generated by the second laser generator is filtered by the second excitation light filter and reflected by the beam splitter; wherein the light chopper allows light generated by one laser generator to go through while blocking laser generated by another laser generator at a given time; wherein the light allowed to pass through is reflected by the second reflecting mirror, passes through the aperture of the aperture-containing mirror and is focused on the microarray by the excitation objective lens; wherein emission light from the microarray is collimated by the excitation objective lens, and reflected by the aperture-containing mirror; and wherein the reflected emission light is filtered by the emission light filter, becomes focused by the emission objective lens, passes the pinhole and gets detected by the detector.

Scanning Platform of the Microarray Scanner

The scanning platform of the microarray scanner moves the microarray relative to the optical system so that the microarray can be scanned. The scanning platform described herein may comprise a novel scanning platform described in patent application entitled "High Speed Scanning Platform for Microarray Scanner,", incorporated entirely herein by reference.

In some embodiments, the scanning platform p comprises a stage for placing a microarray, wherein the stage is controlled by a driving mechanism comprising a wheel and a flexible metal strip winding around the wheel. Generally, the flexible metal strip winds around the wheel at least once. Two regions of the flexible metal strip, typically at opposite ends of a region of the flexible metal strip that winds around the wheel, are affixed to the stage. The wheel rotates around a rotation axis, and pulls the flexible metal strip. The flexible metal strip in turn pulls the stage, resulting in a linear movement of the stage. The rotary movement of the wheel is thus converted into linear movement through the flexible metal strip. Because the wheel can rotate either clockwise of counterclockwise, the stage can move in either direction.

The two regions of the flexible metal strip that are affixed to the stage can be affixed to the stage in any suitable manner. For example, the two regions can be affixed to two corners of the same end of the stage. The two regions can be affixed to the stage by any method known in the art. In some embodiments, one of the two regions of the flexible metal strip that are affixed to the stage is releasably affixed to the stage. The flexible metal strip may further comprise a prefastening region extending beyond the region that is releasably affixed to the stage. The end of the prefastening region may also be affixed to the stage. The prefastening region, in combination with the region of the flexible metal strip that is releasably affixed to the stage, can serve to adjust the tension of the region of the metal strip that winds around the wheel.

The flexible metal strip is generally made of a material with sufficient flexibility. Suitable materials for the flexible metal strip include, but are not limited to, steel, spring steel, and alloy steel. The flexible metal strip is generally very thin. Suitable thickness of the flexible metal strip include, but is not limited to, about 0.05 mm and 0.5 mm, such as between about 0.05 mm and about 1 mm.

In some embodiments, the wheel of the flexible metal strip/wheel driving mechanism is coupled to a servo motor with low inertia.

In some embodiments, the scanning platform comprises stage for placing the microarray to be scanned, wherein the stage (and the microarray placed thereon) can move in any desired manner in a two-dimensional plane. Specifically, the stage of the scanning platform is coupled to two driving mechanisms. One driving mechanism (the scanning driving mechanism) controls the repetitive movement of the stage in the direction(s) of scanning. Another driving mechanism (the forwarding driving mechanism) controls the forward movement of the stage in a direction that is different from (such as perpendicular to) the scanning direction. The two driving mechanisms work together to allow the whole microarray to be scanned.

In some embodiments, the first driving mechanism, i.e., the scanning driving mechanism, comprises a wheel and a flexible metal strip winding around the wheel, wherein two regions of the flexible metal strip are affixed to the stage so that rotation of the wheel moves the stage. The flexible metal strip/wheel driving mechanism described herein provides high speed and high precision of repetitivity, and is thus particularly useful for controlling the repetitive movement of the stage in the scanning direction in a high resolution microarray scanner.

On the other hand, the speed of the forward movement of the stage/microarray does not need to be very high, but its precision of repetitivity must be high. Accordingly, the forward driving mechanism can comprise a lead screw (such as a lead screw coupled to a stepper motor). In some embodiments, the lead screw is connected to a motor via a connecting rod.

In some embodiments, the stage is positioned on top of the scanning driving mechanism, which is in turn positioned on top of the forwarding driving mechanism. During scanning, the stage (along with the microarray placed thereon) moves relative to the scanning driving mechanism in the scanning direction. The scanning driving mechanism (along with the stage and the microarray chip placed thereon) moves in the direction of the forward movement.

In some embodiments, the scanning platform comprises a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail. In some embodiments, the scanning platform comprises a base member including a first guiding rail; a first slider that is slidably coupled to the first guiding rail, wherein the first slider includes a second guiding rail that is perpendicular to the first guiding rail; a forwarding driving mechanism coupled to the first slider which slidably moves the first slider along the first guiding rail; a second slider that is slidably coupled to the second guiding rail; a stage mounted on the second slider; and a scanning driving mechanism coupled to the stage which slidably moves the stage and the second slider along the second guiding rail.

In some embodiments, the scanning driving mechanism comprises a wheel and a flexible metal strip winding around the wheel, wherein two regions of the flexible metal strip are affixed to the stage so that rotation of the wheel moves the stage. In some embodiments, one of the two regions of the flexible metal strip is releasably affixed to the stage. In some embodiments, the flexible metal strip further comprises a prefastening region extending beyond the region that is releasably affixed to the stage.

In some embodiments, the scanning driving mechanism is actuated by, i.e., coupled to, a servo motor (such as a servo motor with low inertia). The scanning driving mechanism (including the motor) may be mounted on the slider and moves along the first guiding rail in the direction of forward movement.

The forwarding driving mechanism may comprise a lead screw coupled to a motor (such as a stepper motor). In some embodiments, the lead screw is connected to the motor via a connecting rod.

The first guiding rail on the base member may either be mounted on the base member or be an integral part of the base member. Similarly, the second guiding rail on the slider may either be mounted on the slider (or the first slider) or be an integral part of the base member. The guiding rails can be made of any materials that are grind-resistant, such as polished stainless steel. The guiding rails may further be coated with polytetrafluoroethylene (PTFE) (commonly available under the trade name TEFLON).

The base member and the slider may further include brackets. The first and second guiding rails extend longitudinally between these brackets. Specifically, the first guiding rail includes a first end and a second end. The first end is fixedly coupled to a first bracket on the base member and the second end fixedly coupled to a second bracket on the base member. The ends of the second guiding rail may be fixedly coupled to brackets on the slider in a similar manner.

In some embodiments, the scanning platform further comprises mechanical switches and photoswitches in the scanning direction and/or the forwarding direction. The mechanical switch may be positioned on the first or second guiding rail to limit (or alter the direction of) movement of the slider or stage. The photoswitch may be used for determining the position of the slider/stage. In some embodiments, the scanning platform comprises an optical grating for determining the position of the stage.

In one embodiment, the scanning platform comprises a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism. In another embodiment, the scanning platform comprises a base member including a first guiding rail; a first slider that is slidably coupled to the first guiding rail and wherein the first slider includes a second guiding rail that is perpendicular to the second guiding rail; a lead screw coupled to the first slider; a stepper motor coupled to the lead screw; a second slider that is slidably coupled to the second guiding rail; a stage mounted on the second slider, a scanning driving mechanism comprising a wheel and a flexible metal strip winding around the wheel, wherein two regions of the flexible metal strip are affixed to the stage so that rotation of the wheel moves the stage and the second slider; and a servo motor coupled to the scanning driving mechanism.

Data Processing System

The data processing system of the microarray scanner transforms light signals detected by the detector of the optical system into digital and/or imagining data. Components (in the forms of hardware, software, or combinations thereof) in the data processing system are largely conventional and of the type used in other types of laser microarray scanners. For example, there can be an amplifier filter circuit and corresponding analog-to-digital converter (AD converter) connected to the detector (such as PMT). The digital signals generated by the AD converter can then be sent to a computer via a data interface. The computer processes the data to produce a normalized signal intensity and background intensity for each feature of the microarray. These intensities can then be further processed in order to produce textual, graphical, or a combination of textual and graphical displays of the data. The computer may also provide software for further interpreting the data to generate experimental or clinical results. The raw and/or processed data can be stored in a computer-readable medium, transferred to an intercommunicating entity via electronic signals, printed on a human readable format, or otherwise made available for further use.

The data processing system may also comprise a DA converter connected to the detector (such as the PMT) that provides feedback control of the output signal from the detector (such as the PMT). In some embodiments, the data processing system also comprises an amplifier filter circuit and an AD converter connected to a light intensity detector described herein.

Traditional microarray scanners readily detect bright light spots on a microarray, but were not good at separating weak light spots with background signals. Use of a DA converter to provide continuous feedback control of the detector (such as PMT), optionally combined with the use of attenuators to continuously control the excitation light power, greatly increases the sensitivity of the scanner. Furthermore, the scanner of the present invention provides a wide range of dynamics, thereby provides images and data with high quality.

EXEMPLARY EMBODIMENT OF THE INVENTION

Figure 1:
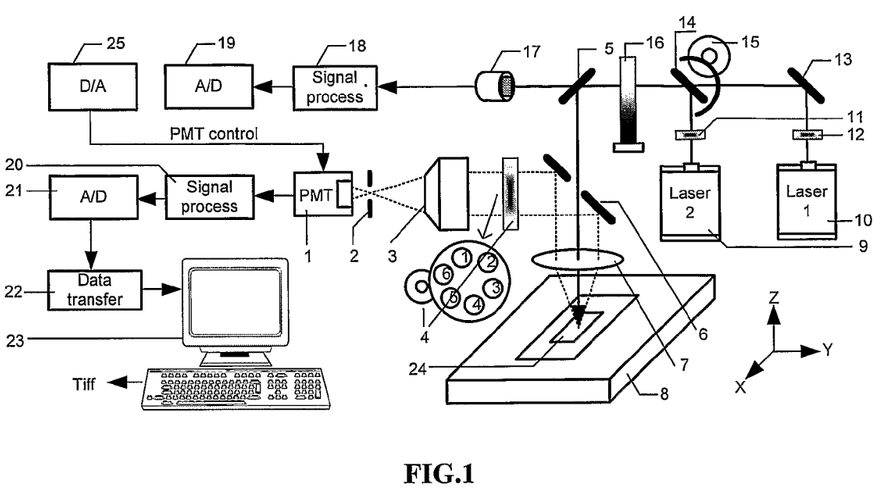
FIG. 1 is a schematic diagram of an exemplary microarray scanner of the present invention.

FIG. 1 shows one embodiment of the present invention. First laser generator 10 generates laser light, which passes laser light filter 12, becomes reflected by reflecting mirror 13, and transmits through beam splitter 14. Second laser generator 9 generates laser light, which passes laser light filter 11 and becomes reflected by beamsplitter 14. Light chopper 15 was placed next to beam splitter 14 to allow either laser generated by first laser generator 9 or by second laser generator 10 to go through. The selected laser light becomes attenuated by attenuator 16. The attenuated light hits proportional reflecting mirror 5. In order to determine the intensity of the excitation light, there is a light intensity detector 17 optically positioned to detect light transmitted by proportional reflecting mirror 5. Light signal detected by the light intensity detector is amplified by amplifier filter circuit 18 and converted to digital signals by AD converter 19. Light reflected by proportional reflecting mirror 5 directly passes the aperture of aperture-containing reflecting mirror 6 and becomes focused on the surface of microarray 24 placed on platform 8 via excitation objective lens 7.

Light emitted from the microarray 24 becomes collimated by excitation objective lens 7 and is reflected by aperture-containing reflecting mirror 6. The reflected light passes complex light filter 4 and fluorescent objective lens 3. Pinhole 2 only allows focused light to pass through, which is detected by PMT 1. Signals collected by PMT 1 is amplified by amplifier filter circuit 20 and converted into digital signals by AD converter 21. Data obtained thereof is then introduced to computer processing unit 23 to generate TIFF files through data interface 22. PMT 1 is also connected to DA converter 25, which provides feedback control to the PMT. In this exemplary embodiment, USB was used for data communication.

Figure 2:
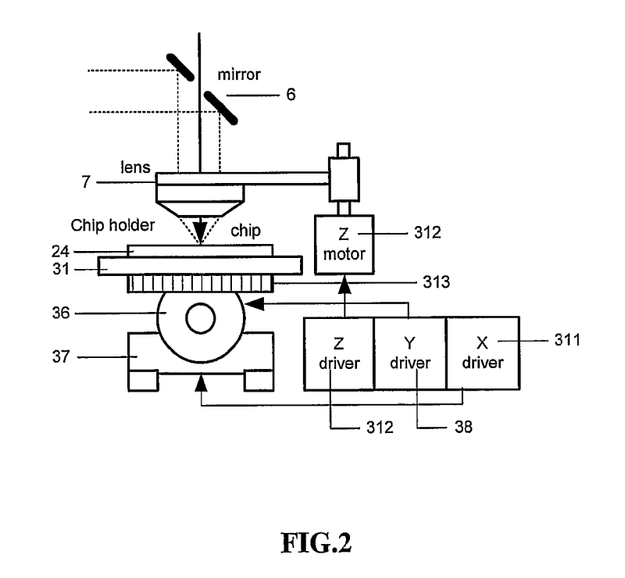
FIG. 2 is a schematic diagram of the scanning platform portion of an exemplary microarray scanner of the present invention.

FIG. 2 shows a schematic diagram of the scanning platform portion of an exemplary microarray scanner of the present invention. As shown in FIG. 2, microarray slide 24 is placed on top of stage 31, which is part of the scanning platform. Stage 31 moves along the Y-axis under the control of scanning driving mechanism 36, which is actuated by Y-driving servo motor 318. The scanning driving mechanism drives the repetitive movement of the stage in the scanning directions, and properly controls the positional precision of the stage movement. Scanning driving mechanism is placed on top of slider 37, which is controlled by forwarding driving mechanism driven by X-driving stepper motor 311 and moves along the X-axis. There is also a Z-driving stepper motor, which controls the movement of the excitation objective lens along the Z-axis in order to focus the light.

During scanning, slider 37 moves along the X-axis in intervals of one resolution distance. In the mean time, stage 31 moves relative to the slider along the Y-axis, in intervals of one scanning width distance. The positioning of the stage along the Y-axis is controlled by optical grating 313, which counts the numbers and controls the position of scanning. When stage 31 has moved a designated distance along the scanning direction (i.e., the Y axis), the Y-driving servo motor 38 switches direction and drives the movement of the stage in an opposite direction along the Y-axis. In the meanwhile, slider 37 moves one resolution distance forward, allowing a separate row of the microarray to be scanned. The same steps repeat several times until slider 37 has reached its designated moving distance.

The microarray scanner of the exemplary embodiment can scan one or more microarray chips within the range of 22 mm×72 mm. In this embodiment, each of the two laser generators generated laser light of 532 nm and 635 nm, respectively. The two laser generators, used in combination with the complex emission filter, provided 6 different light channels, and four different kinds of resolutions (5 µm, 10 µm, 20 µm, 40 µm, respectively). A single-channel scanning of each microarray chip took about 6-8 minutes. Detection sensitivity was less than 0.1 fluorescent molecules per µm².

Figure 3:
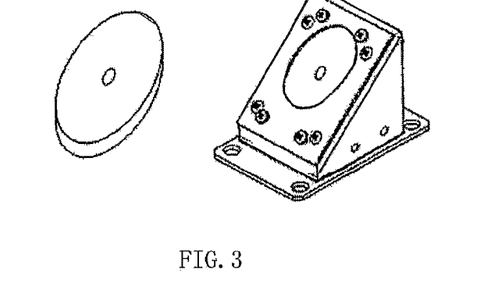
FIG. 3 is a schematic diagram of an exemplary aperture-containing reflecting mirror of the microarray scanner of the present invention.

FIG. 3 shows one embodiment of the aperture-containing reflecting mirror described herein for the optical system of the microarray scanner. The mirror has an oval shape and is tiled 45° relative to the horizontal surface. A circular aperture with a 3 mm diameter is present at the center of the mirror, which allows excitation light to pass through without blockage. One side of the mirror has a reflecting surface for reflecting the emission light. In this arrangement, the excitation light path is perpendicular to the collection light path, and does not interfere with each other.

Figure 4:
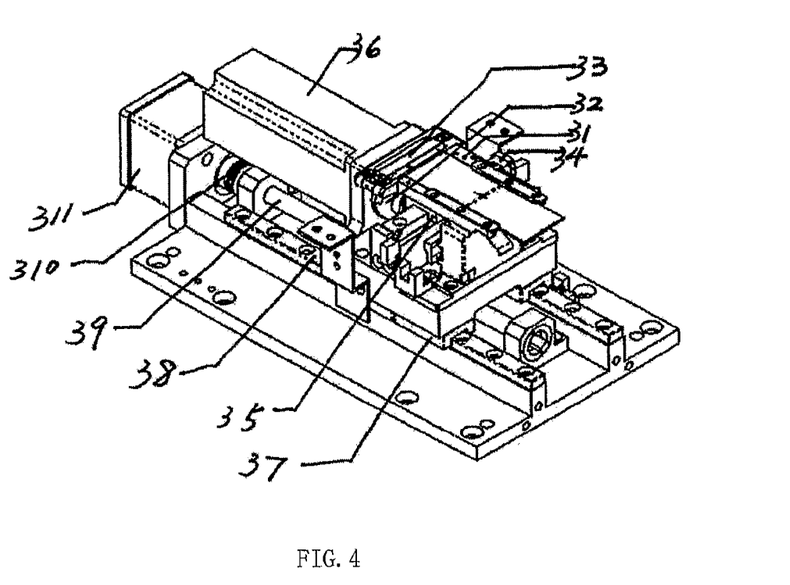
FIG. 4 is a schematic diagram of an exemplary scanning platform of the microarray scanner of the present invention.

FIG. 4 shows one embodiment of a scanning platform used in an exemplary laser microarray scanning device. As shown in FIG. 4, stage 31 is mounted on second slider 35, which is slidably coupled to second guiding rail 34. Thin steel strip 33 is affixed to stage 31 and winds around wheel 32. Scanning motor 36 drives the thin steel strip/wheel system, which slidably moves second slider 35/stage along second guiding rail 34. Second guiding rail 34, wheel 32, thin steel strip 33 and scanning motor 36 thus together make the scanning driving mechanism that moves the stage. Second guiding rail 34 is positioned on first slider 37. Stage 31, controlled by the scanning driving mechanism, moves relative to first slider 37 in the direction of scanning.

First guiding rail 38, lead screw 39, connecting rod 310 and stepper motor 311 together make the forwarding driving mechanism. Under the control of the forwarding driving mechanism, first slider 37, on which the scanning driving mechanism is positioned, moves forward in a direction that is perpendicular to the scanning direction. During scanning, the stage moves in both the forwarding direction and the scanning direction, and thus allows the whole microarray be scanned at high speed and with high precision.

Figure 5:
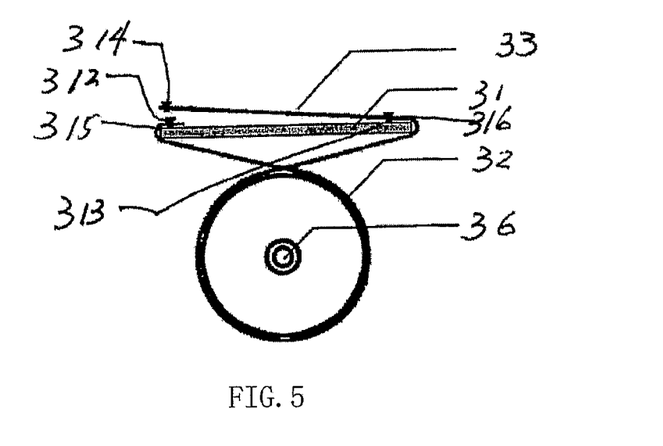
FIG. 5 is a schematic diagram f an exemplary thin steel strip/wheel driving system of the microarray scanner of the present invention.

FIG. 5 shows one embodiment of the linear driving system of the present invention. The driving system comprises thin steel strip 33 and wheel 32. Wheel 32 is actuated by low inertia servo motor 36, and can rotate clockwise or counterclockwise. Thin steel strip 33 winds around wheel 32 once. Region 315 and region 316 of the flexible metal strip, which are at opposite ends of the metal strip region that winds around the wheel, are affixed to two corners of the same end of stage 31 by screws 312 and 313. Region 316 is releasably affixed to the stage. In this embodiment, the flexible metal strip extends beyond region 316, with its end further affixed on the stage by screw 314. The portion of the flexible metal strip between screw 313 and 314 serves a prefastening function, that is, the tension of the strip around the wheel can be changed by adjusting the prefastening region of the flexible metal strip. The driving mechanism converts the rotary movement of wheel 32 into repetitive linear movement through use of thin steel strip 33. The system as shown can achieve a scanning speed of 10-20 Hz (within a 10 mm range). Furthermore, it provides high precision of repetitivity, thereby solves the problem associated with traditional belt-driven mechanisms.

Although the foregoing invention has been described in some detail by way of illustration and example for purpose of clarity and understanding, it will be apparent to those of skill in the art that certain changes and modifications can be practiced. Therefore, the description and examples should not be construed as limiting the scope of the invention, which is delineated by the appended claims. All the drawings are illustrated schematically. Angles and dimensions are not to scale.

What is claimed is:

1. A laser microarray scanner comprising an optical system, a scanning platform, and a data processing system, wherein the optical system comprises an aperture-containing reflecting mirror comprising an aperture and a reflecting surface, wherein the aperture on the aperture-containing reflecting mirror allows an excitation light to pass through and wherein the reflecting surface of the aperture-containing reflecting mirror allows emission light from a microarray to be reflected, and wherein the scanning driving mechanism comprises a wheel and a flexible metal strip winding around the wheel, wherein two regions of the stage are affixed to the stage so that rotation of the wheel moves the stage.

2. The laser microarray scanner of claim 1, wherein the optical system further comprises an excitation objective lens for focusing the excitation light passing through the aperture-containing reflecting mirror.

3. The laser microarray scanner of claim 2, wherein the optical system further comprises: a light forwarding system comprising a first laser generator; a first reflecting mirror that reflects light generated by the first laser generator, a second laser generator; a beam splitter that transmits light reflected by the first reflecting mirror and reflects light generated by the second laser generator; a light chopper that allows light generated by one laser generator to go through while blocking light generated by another laser generator at a given time; and a second reflecting mirror that reflects the light allowed to go through, wherein light reflected by the second reflecting mirror passes through the aperture of the aperture-containing reflecting mirror; and a light collection system comprising an emission filter optically positioned behind the aperture-containing reflecting mirror, an emission objective lens optically positioned behind the emission filter, a pinhole optically positioned behind the emission objective lens, and a detector, wherein emission light reflected by the aperture-containing reflecting mirror passes the emission filter, emission objective lens, and pinhole sequentially before it reaches the detector.

4. The laser microarray scanner of claim 1, wherein the optical system further comprises a light forwarding system for generating the excitation light.

5. The laser microarray scanner of claim 4, wherein the light forwarding system of the optical system comprises a first laser generator, a second laser generator, a beam splitter, and a light chopper, wherein the beam splitter transmits laser light generated by the first laser generator and reflects laser light generated by the second laser generator, and wherein the light chopper allows laser light generated by one laser generator to go through while blocking laser light generated by another laser generator at each time.

6. The laser microarray scanner of claim 5, wherein the light forwarding system of the optical system further comprises a first reflecting mirror optically positioned between the first laser generator and the beam splitter and a second reflecting mirror optically positioned between the beam splitter and the aperture-containing reflecting mirror, wherein light generated by the first laser generator is first reflected by the first reflecting mirror before it is transmitted by the beam splitter, and wherein light coming from the beam splitter is first reflected by the second reflecting mirror before it passes through the aperture of the aperture-containing reflecting mirror.

7. The laser microarray scanner of claim 5, wherein the light forwarding system of the optical system further comprises matching light filter optically positioned in front of at least one of the two laser generators.

8. The laser microarray scanner of claim 5, wherein the light forwarding system of the optical system further comprises an attenuator, wherein the attenuator is optically positioned behind the beam splitter.

9. The laser microarray scanner of claim 1, wherein the optical system further comprises a light collection system for collecting the emission light, wherein the light collection system comprises a detector and an emission objective lens optically positioned between the detector and the aperture-containing reflecting mirror.

10. The laser microarray scanner of claim 9, wherein the detector is a photomultiplier tube.

11. The laser microarray scanner of claim 9, wherein the light collection system of the optical system further comprises a pinhole optically positioned between the emission objective lens and the detector.

12. The laser microarray scanner of claim 11, wherein the light collection system of the optical system further comprises an emission light filter optically positioned between the aperture-containing reflecting mirror and the emission objective lens.

13. The laser microarray scanner of claim 12, wherein the emission light filter comprises two or more light filters for filtering light of different wavelengths.

14. The laser microarray scanner of claim 1, wherein the scanning platform comprises a stage coupled to a scanning driving mechanism that drives movement of the stage in the scanning direction and a forwarding driving mechanism that drives movement of the stage in the forwarding direction.

15. A laser microarray scanner comprising an optical system, a scanning platform, and a data processing system, wherein the scanning platform comprises a stage for placing a microarray, wherein the stage is controlled by a first driving mechanism comprising a wheel and a flexible metal strip winding around the wheel, wherein two regions of the flexible metal strip are affixed to the stage so that rotation of the wheel moves the stage.

16. The laser microarray scanner of claim 15, wherein the wheel is actuated by a servo motor with low inertia.

17. The laser microarray scanner of claim 15, wherein the scanning platform further comprises a second driving mechanism, wherein the first driving mechanism moves the stage in a scanning direction, and wherein the second driving mechanism moves the stage in a forwarding direction that is different from the scanning direction.

18. The laser microarray scanner of claim 17, wherein the second driving mechanism moves the stage in a forwarding direction that is perpendicular to the scanning direction.

19. The laser microarray scanner of claim 17, wherein the first driving mechanism is positioned below the stage and above the second driving mechanism.

20. The laser microarray scanner of claim 17, wherein the second driving mechanism comprises a lead screw coupled to a stepper motor.

21. A laser microarray scanner comprising an optical system, a scanning platform, and a data processing system, wherein the scanning platform comprises a base member including a first guiding rail; a slider that is slidably coupled to the first guiding rail, wherein the slider includes a second guiding rail that is perpendicular to the first guiding rail; a forwarding driving mechanism coupled to the slider which slidably moves the slider along the first guiding rail; a stage that is slidably coupled to the second guiding rail; and a scanning driving mechanism coupled to the stage which slidably moves the stage along the second guiding rail, and wherein the scanning driving mechanism of the scanning platform comprises a wheel and a flexible metal strip winding around the wheel, wherein two regions of the flexible metal strip are affixed to the stage so that rotation of the wheel moves the stage.

22. The laser microarray scanner of claim 21, wherein the scanning driving mechanism is actuated by a servo motor with low inertia.

23. The laser microarray scanner of claim 21, wherein the scanning driving mechanism is mounted on the slider.

24. The laser microarray scanner of claim 21, wherein the forwarding driving mechanism comprises a lead screw coupled to a stepper motor.

25. A laser microarray scanner comprising an optical system, a scanning platform, and a data processing system, wherein the scanning platform comprises a base member including a first guiding rail; a slider that is slidably coupled to the first guiding rail and wherein the slider includes a second guiding rail that is perpendicular to the second guiding rail; a lead screw coupled to the slider; a stepper motor coupled to the lead screw; a stage that is slidably coupled to the second guiding rail; a scanning driving mechanism comprising a wheel and a flexible metal strip winding around the wheel, wherein two regions of the flexible metal strip are affixed to the stage so that rotation of the wheel moves the stage; and a servo motor coupled to the scanning driving mechanism.

26. The laser microarray scanner of claim 25, wherein the scanning driving mechanism is mounted on the slider.

27. The laser microarray scanner of claim 25, wherein the optical system comprises a light forwarding system comprising a first laser generator, a second laser generator, a beam splitter, and a light chopper, wherein the beam splitter transmits laser light generated by the first laser generator and reflects laser light generated by the second laser generator, and wherein the light chopper allows laser light generated by one laser generator to go through while blocking laser light generated by another laser generator at each time.

28. The laser microarray scanner of claim 25, wherein the optical system comprises a light collection system comprising an emission filter, an emission objective lens optically positioned behind the emission filter, a pinhole optically positioned behind the emission objective lens, and a detector optically positioned behind the pinhole, wherein emission light passes the emission filter, emission objective lens, and pinhole sequentially before it reaches the detector.

* * * * *